United States Patent
Chuang (10) Patent No.: US 10,828,002 B2
(45) Date of Patent: Nov. 10, 2020

(54) X-RAY DETECTOR AND METHOD FOR USING X-RAY DETECTOR TO CAPTURE IMAGE

(71) Applicant: HANNSTOUCH SOLUTION INCORPORATED, Tainan (TW)

(72) Inventor: Che-Yu Chuang, Tainan (TW)

(73) Assignee: HANNSTOUCH SOLUTION INCORPORATED, Tainan (TW)

( * ) Notice: Subject to any disclaimer, the term of this patent is extended or adjusted under 35 U.S.C. 154(b) by 133 days.

(21) Appl. No.: 16/219,971

(22) Filed: Dec. 14, 2018

(65) Prior Publication Data

US 2020/0187890 A1 Jun. 18, 2020

(51) Int. Cl.
*A61B 6/00* (2006.01)
*G01T 1/24* (2006.01)
*G01T 1/20* (2006.01)

(52) U.S. Cl.
CPC .......... *A61B 6/5258* (2013.01); *A61B 6/4233* (2013.01); *A61B 6/585* (2013.01); *G01T 1/247* (2013.01); *G01T 1/2018* (2013.01)

(58) Field of Classification Search
CPC ..... G01T 1/247; G01T 1/2018; A61B 6/5258; A61B 6/4233; A61B 6/585
See application file for complete search history.

(56) References Cited

U.S. PATENT DOCUMENTS

2012/0189100 A1* 7/2012 Liu ................... G01T 1/247
378/62
2015/0146846 A1* 5/2015 Lee ................... H04N 5/3597
378/31

\* cited by examiner

*Primary Examiner* — David P Porta
*Assistant Examiner* — Meenakshi S Sahu
(74) *Attorney, Agent, or Firm* — CKC & Partners Co., LLC (57) ABSTRACT

An X-ray detector includes a substrate, plural signal lines, plural scan lines, plural sensing units, and a first active device. The signal lines are disposed on the substrate. The scan lines are disposed on the substrate and intersecting with the signal lines. The sensing units are electrically connected to the signal lines and the scan lines. The first active device has a first terminal, a second terminal, and a control terminal configured to modulate a conduction between the first terminal and the second terminal. The first terminal of the first active device is connected to a first one of the signal lines, and the second terminal of the first active device is connected to a second one of the signal lines.

18 Claims, 11 Drawing Sheets

X-RAY DETECTOR AND METHOD FOR USING X-RAY DETECTOR TO CAPTURE IMAGE

BACKGROUND

Field of Invention

The present invention relates to an X-ray detector and a method for using an X-ray detector to capture an image.

Description of Related Art

X-ray digital photography has been widely used in the field of medical imaging diagnosis. In various X-ray digital photography equipment, X-ray detectors play an indispensable key in the imaging acquisition process of the entire image. The imaging process of an X-ray detector has a process from "X-ray" to "visible light," and to "electron." During capturing images, X-rays are first incident on a scintillator layer on an upper surface of the X-ray sensor, which converts the incident X-rays into visible light. The visible light activates a photodiode of the X-ray sensor to generate electrons, which are then collected and transformed into appropriate signals that can be read to obtain a digital image. The digital image can be adjusted by a variety of digital image processing easily.

During the operation of the X-ray detector, residual charges may remain in the photodiode, such that the obtained image may be affected by a residual image. For example, the present captured image is superimposed with the residual information of the previous captured image, which influences the image quality. Digital image processing can moderately correct this image, but the correction effect is limited. As such, how to effectively solve the problem of the residual image in the X-ray image sensor and improve the image quality is a problem to be solved.

SUMMARY

In some embodiments of the present invention, by improving the uniformity of charge distribution, the difference between the amounts of the residual charges at plural locations is reduced. Furthermore, by uniformly adjusting the respective pixels of the image, the image quality is improved.

According to some embodiments of the present invention, an X-ray detector includes a substrate, plural signal lines, plural scan lines, plural sensing units, and a first active device. The signal lines are disposed on the substrate. The scan lines are disposed on the substrate and intersecting with the signal lines. The sensing units are electrically connected to the signal lines and the scan lines. The first active device has a first terminal, a second terminal, and a control terminal configured to modulate a conduction between the first terminal and the second terminal. The first terminal of the first active device is connected to a first one of the signal lines, and the second terminal of the first active device is connected to a second one of the signal lines.

In some embodiments, the X-ray detector further includes a control signal line and a control circuit. The control signal line connects the control terminal of the first active device to the control circuit.

In some embodiments, the signal lines are connected to the control circuit.

In some embodiments, the X-ray detector further includes a second active device having a first terminal, a second terminal, and a control terminal configured to modulate a conduction between the first terminal of the second active device and the second terminal of the second active device. The first terminal of the second active device is connected to the second one of the signal lines, and the second terminal of the second active device is connected to a third one of the signal lines.

In some embodiments, the X-ray detector further includes a control signal line connecting the control terminal of the first active device and the control terminal of the second active device.

In some embodiments, the X-ray detector further includes a third active device having a first terminal, a second terminal, and a control terminal configured to modulate a conduction between the first terminal of the third active device and the second terminal of the third active device. The first terminal of the third active device is connected to the first one of the signal lines, and the second terminal of the third active device is connected to a ground potential.

In some embodiments, the X-ray detector further includes a control signal line and a control circuit. The control signal line connects the control terminal of the third active device to the control circuit.

In some embodiments, each of the sensing units includes a light sensing element.

In some embodiments, the X-ray detector further includes an X-ray conversion layer. The sensing units are between the X-ray conversion layer and the substrate.

In some embodiments, the substrate has an array area and a peripheral area at at least one side of the array area, the sensing units are over the array area of the substrate, and the first active device is over the peripheral area of the substrate.

According to some embodiments of the present invention, an X-ray detector includes a substrate, plural signal lines, plural scan lines, plural sensing units, and a control circuit. The signal lines are disposed on the substrate. The scan lines are disposed on the substrate and intersecting with the signal lines. The sensing units are electrically connected to the signal lines and the scan lines. The control circuit is connected between the signal lines. The control circuit is configured to establish an electrical conduction between a first one of the signal lines and a second one of the signal lines at a first timing.

In some embodiments, the control circuit is configured to ground the first one of the signal lines at a second timing, in which the first timing is different from the second timing.

In some embodiments, the control circuit is disposed on the substrate.

According to some embodiments of the present invention, a method for capturing an image by an X-ray detector is provided. The method includes establishing an electrical conduction between a first electrode of a first light sensing element and a second electrode of a second light sensing element; and detecting light by using the first light sensing element and the second light sensing element to obtained an image.

In some embodiments, the method further includes performing a correction process to the image.

In some embodiments, the method further includes grounding the first and second electrodes before establishing the electrical conduction between the first and the second electrodes.

In some embodiments, the first and second electrodes are not grounded when establishing the electrical conduction between the first and second electrodes.

In some embodiments, the method further includes terminating the electrical conduction between the first and second electrodes before detecting the light by the first light sensing element and the second light sensing element.

In some embodiments, the method further includes establishing an electrical conduction between a third electrode of a third light sensing element and the second electrode of the second light sensing element.

In some embodiments, establishing the electrical conduction between the first and second electrodes and establishing the electrical conduction between the second and third electrodes include turning on a first active device and a second active device, wherein the first active device is connected between the first electrode and the second electrode, and the second active device is connected between the second electrode and the third electrode.

BRIEF DESCRIPTION OF THE DRAWINGS

The invention can be more fully understood by reading the following detailed description of the embodiment, with reference made to the accompanying drawings as follows.

DETAILED DESCRIPTION

Reference will now be made in detail to the present embodiments of the invention, examples of which are illustrated in the accompanying drawings. Wherever possible, the same reference numbers are used in the drawings and the description to refer to the same or like parts.

Figure 1A:
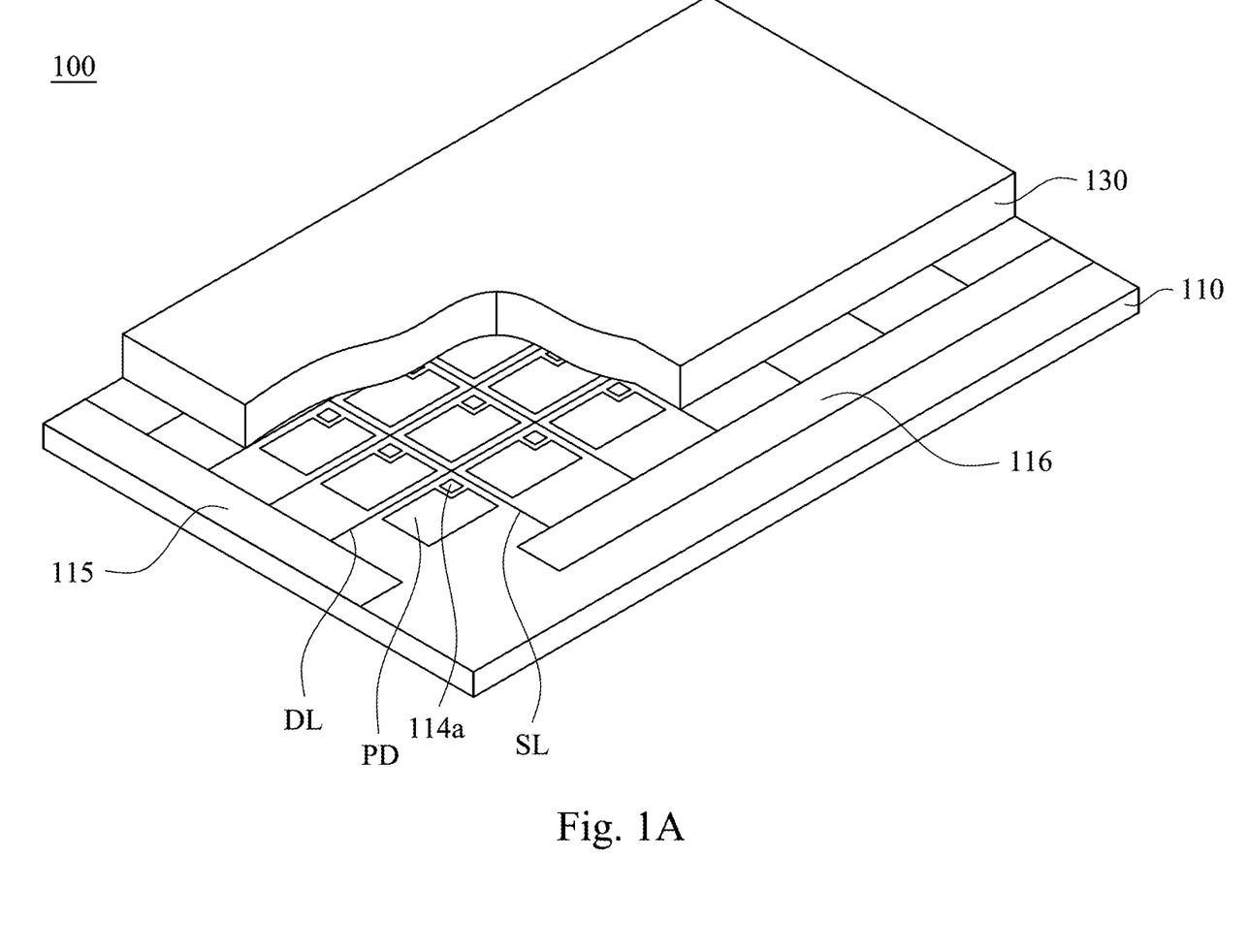
FIG. 1A is a schematic view of an X-ray detector according to some embodiments of the invention.
Figure 1B:
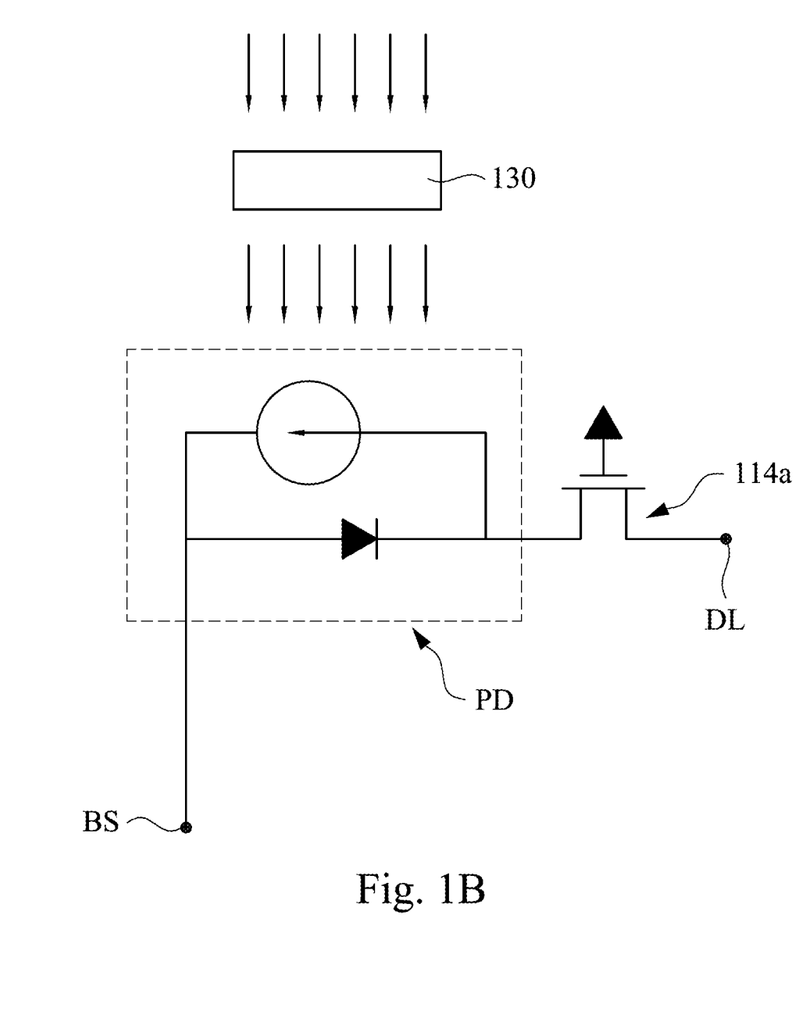
FIG. 1B is an operation schematic view of an X-ray detector according to some embodiments of the invention.

FIG. 1A is a schematic view of an X-ray detector 100 according to some embodiments of the invention. FIG. 1B is an operation schematic view of an X-ray detector 100 according to some embodiments of the invention. Reference is made to both FIG. 1A and FIG. 1B. The X-ray detector 100 includes an active device array substrate 110 and an X-ray conversion layer 130. The X-ray conversion layer 130 is disposed on the active device array substrate 110. In the present embodiments, the X-ray conversion layer 130 may convert electrons into light. For example, the X-ray conversion layer 130 includes a scintillator to convert X-ray into light (e.g., visible light). The active device array substrate 110 includes plural signal lines DL, plural scan lines SL, plural active devices 114a, and light-sensing devices PD.

The light generated by the X-ray conversion layer 130 is received by the light-sensing devices PD and converted into positive/negative charges. Under suitable bias, the positive/negative charges flow to the active devices 114a as electric current. The conduction of the active devices 114a is controlled by the scan lines SL, such that the electric current generated by the light-sensing devices PD may flow through the active devices 114a to the signal lines DL, thereby transmitting light-sensing signals. For example, the light-sensing devices PD may be photodiodes. The active device array substrate 110 may further include a signal control circuit 115 and a scan control circuit 116 respectively connected to the signal lines DL and the scan lines SL, so as to retrieve the light-sensing signals and send switching signals to control the active devices 114a.

Figure 2A:
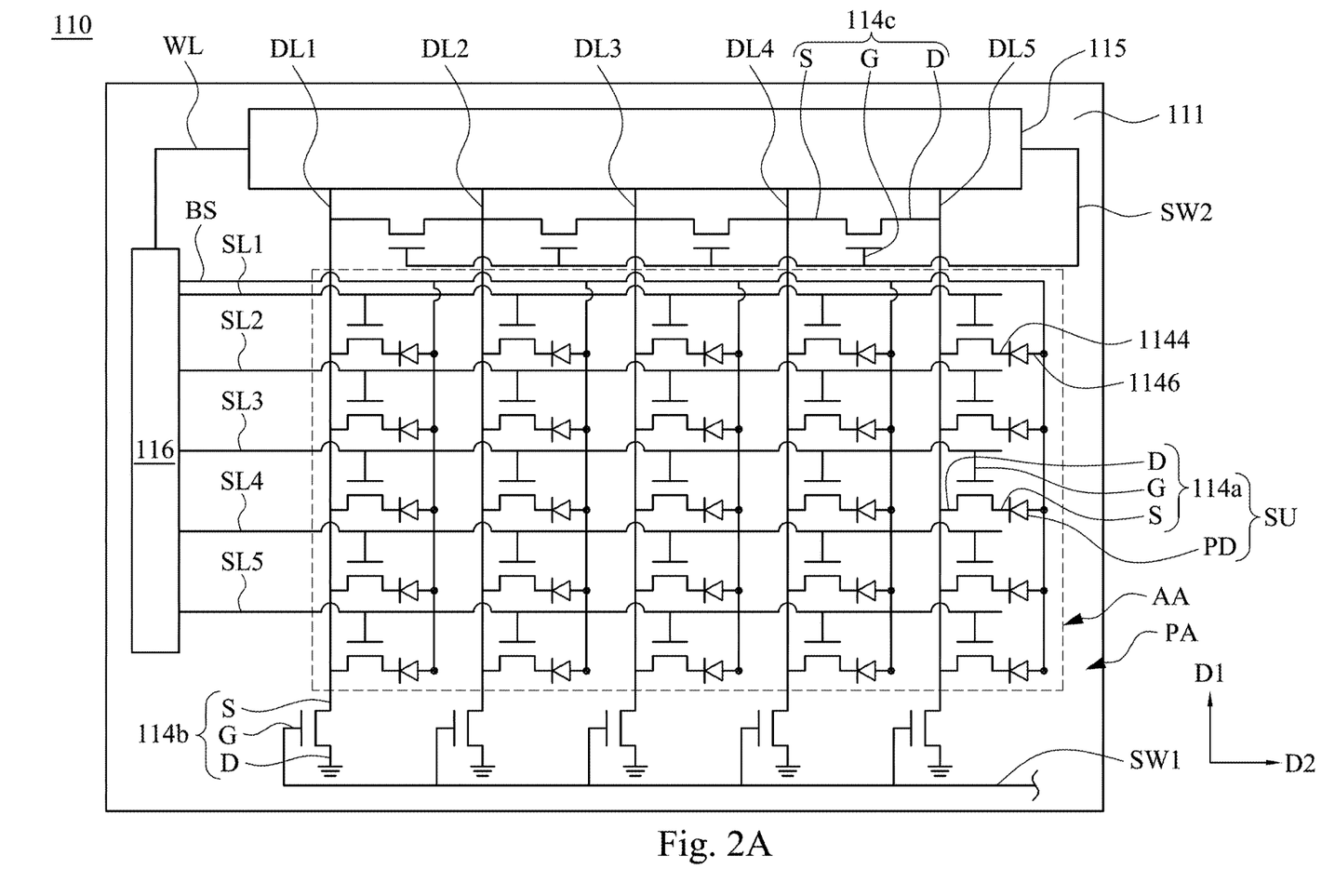
FIG. 2A is a schematic top view of an active device array substrate of an X-ray detector according to some embodiments of the invention.

FIG. 2A is a schematic top view of an active device array substrate 110 of an X-ray detector 100 according to some embodiments of the invention. To be specific, the active device array substrate 110 includes a substrate 111, plural signal lines DL1-DL5, plural scan lines SL1-SL5, plural sensing units SU, a signal control circuit 115, a scan control circuit 116, active devices 114b and 114c, control signal line SW1, SW2, and bias line BS. The substrate 111 has an array area AA and a non-array area (also referred to as a peripheral area) PA, in which the non-array area PA is at at least one side of the array area AA. The sensing units SU are disposed in the array area AA, and the signal control circuit 115, the scan control circuit 116, the active devices 114b and 114c, and the control signal line SW1, SW2 are disposed in the non-array area PA. Herein, the signal lines DL1-DL5 and the scan lines SL1-SL5 extend through the array area AA to the non-array area PA, so as to connect the sensing units SU, the signal control circuit 115, and the scan control circuit 116.

In the present embodiments, the signal lines DL1-DL5 and the scan lines SL1-SL5 are electrically isolated from each other and intersecting with each other. For example, the signal lines DL1-DL5 extends in a first direction D1, and the scan lines SL1-SL5 extends in a second direction D2, which is not parallel with the first direction D1. For example, the first direction D1 is orthogonal to the second direction D2. The signal control circuit 115 and the scan control circuit 116 are respectively connected to the signal lines DL1-DL5 and the scan lines SL1-SL5, so as to control and read signals of the sensing units SU. In some embodiments, the signal control circuit 115 may also referred to as a signal receiver, and the scan control circuit 116 may also referred to as a scan driver.

In some embodiments, each of the sensing units SU includes an active device 114a and the aforementioned light-sensing device PD. Each of the active devices 114a has a first terminal (e.g., the source electrode S), a second terminal (e.g., the drain electrode D), and a control terminal (e.g., the gate electrode G), in which the control terminal (e.g., the gate electrode G) is configured to modulate a conduction between the first terminal (e.g., the source electrode S) and the second terminal (e.g., the drain electrode D).

Figure 2B:
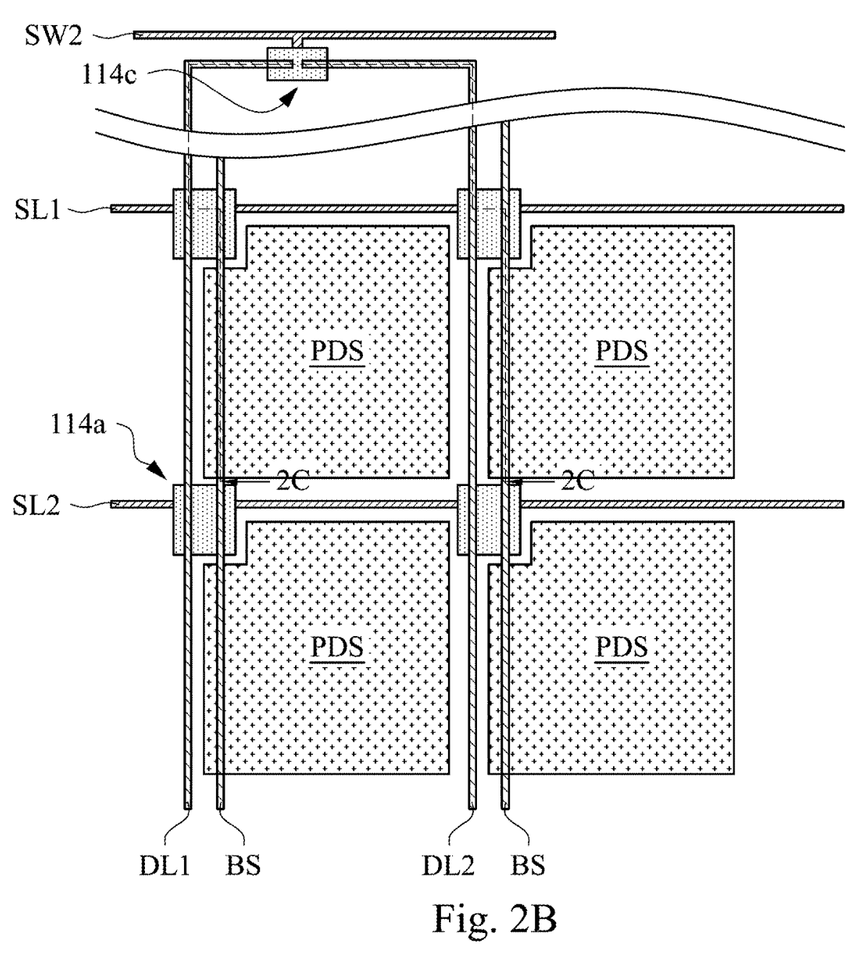
FIG. 2B is a layout of a portion of FIG. 2A.
Figure 2C:
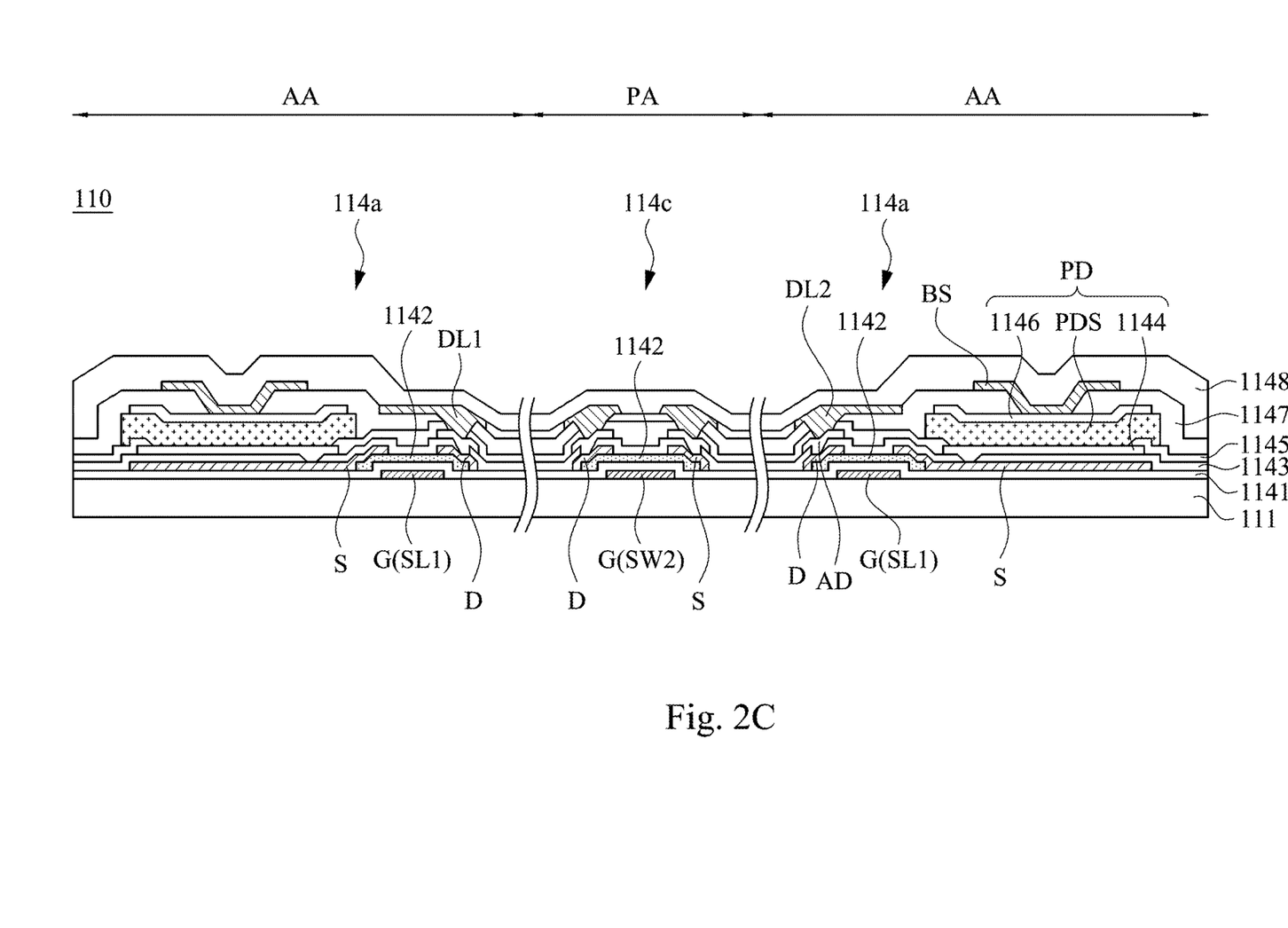
FIG. 2C is a schematic cross-sectional view taken along line 2C-2C of FIG. 2B.

In the present embodiments, the gate electrodes G of the active devices 114a are respectively connected to the scan lines SL1-SL5, the drain electrodes D of the active devices 114a are respectively connected to the signal lines DL1-DL5, and the source electrodes S of the active devices 114a are respectively connected to bottom electrodes 1144 of the light-sensing devices PD (referring to FIG. 2C). Through the configuration, by using the scan control circuit 116 to time-sequentially provide control signals to the scan lines SL1-SL5, the active devices 114a in respective columns are time-sequentially turned on, such that signals detected by the light-sensing device PD in respective columns are time-sequentially transmitted to the signal lines DL1-DL5 through the active devices 114a.

In the present embodiments, each of the active devices 114b and 114c has a source electrode S, a drain electrode D, and a gate electrode G as the configuration of the active devices 114a. The gate electrodes G of the active devices 114b are connected to the control signal line SW1, the drain electrodes D of the active devices 114b are grounded, and the source electrodes D of the active devices 114b are connected to the signal lines DL1-DL5, respectively. Through the configuration, in a certain time range, the active devices 114b are turned on by the control signal line SW1 to ground the signal lines DL1-DL5, and in the time range, the active devices 114a are turned on by the scan lines SL1-SL5 simultaneously or time-sequentially, such that a conduction is established between the light-sensing devices PD and the grounded signal lines DL1-DL5, which in turn will remove residual charges in the light-sensing devices PD. In some embodiments, the control signal line SW1 may be connected to the signal control circuit 115 or the scan control circuit 116 for receiving control signals from the signal control circuit 115 or the scan control circuit 116.

In the present embodiments, the gate electrodes G of the active devices 114c are connected to the control signal line SW2, the source electrodes S and/or the drain electrodes D of the active devices 114c are respectively connected to the signal lines DL1-DL5, and the source electrodes S and/or the drain electrodes D of the active devices 114c are connected with each other. Through the configuration, in a certain time range, the active devices 114c are turned on by the control signal line SW2 to electrically connect the signal lines DL1-DL5 to each other and short the signal lines DL1-DL5, and in the time range, the active devices 114a are turned on by the scan lines SL1-SL5 simultaneously, such that the light-sensing devices PD are shorted, which in turn will make the residual charges in the light-sensing devices PD uniform. In this process, it may be designed that the signal lines DL1-DL5 are not grounded, so as to achieve the purpose of making charge distribution uniform. In some embodiments, the control signal line SW2 may be connected to the signal control circuit 115 or the scan control circuit 116 for receiving control signals from the signal control circuit 115 or the scan control circuit 116. For example, herein, the control signal line SW2 is connected to the signal control circuit 115.

The bias line BS is connected to a terminal of the light-sensing device PD for providing suitable bias, which facilitates the current output of the light-sensing device PD. The bias line BS may be connected to the signal control circuit 115 or the scan control circuit 116 for receiving bias signals from the signal control circuit 115 or the scan control circuit 116. For example, herein, the bias line BS is connected to the scan control circuit 116.

FIG. 2B is a layout of a portion of the active device array substrate 110 of FIG. 2A. FIG. 2C is a schematic cross-sectional view taken along line 2C-2C of FIG. 2B. Reference is made to both FIG. 2B and FIG. 2C. The active device array substrate 110 includes a substrate 111, gate electrodes G, a gate dielectric layer 1141, semiconductor layers 1142, source and drain electrodes S and D, a passivation layer 1143, a bottom electrode 1144, a passivation layer 1145, a light-sensing structure PDS, a top electrode 1146, a passivation layer 1147, signal lines DL1-DL2, bias lines BS, and a passivation layer 1148 over the substrate 111 in a sequence. These features are illustrated in a sequence from bottom to top in the following.

In some embodiments of the present disclosure, the substrate 111 may be rigid substrate, such as glass, acrylic, polyethylene terephthalate (PET), poly(methyl methacrylate)(PMMA), and other suitable material. Alternatively, in some other embodiments, the substrate 111 may also be soft substrate (i.e., flexible substrate), such as plastic film or other suitable materials.

In some embodiments of the present disclosure, the gate electrodes G of the active devices 114a-114c, the scan lines SL1-SL5, and the control signal lines SW1 and SW2 may include suitable conductive material, such as metal, for example, Cu, Mo/Al/Mo, Mo/Al—Nd/Mo, or the like. In some embodiments, the gate electrodes G of the active devices 114a-114c, the scan lines SL1-SL5, and the control signal lines SW1 and SW2 are formed by the same fabrication process. For example, the fabrication process includes disposing a metal layer is over the substrate 111, and patterning the metal layer to form the gate electrodes G of the active devices 114a-114c, the scan lines SL1-SL5, and the control signal lines SW1 and SW2. The scan lines SL1-SL5 connect the gate electrodes G to the scan control circuit 116. In the present embodiments, the control signal lines SW1 and SW2 intersects with the signal lines DL1-DL5. For example, the control signal lines SW1 and SW2 extend along the first direction D1.

The gate dielectric layer 1141 is disposed over the gate electrodes G of the active devices 114a-114c, the scan lines SL1-SL5, and the control signal lines SW1 and SW2. The semiconductor layers 1142 are disposed over the gate dielectric layer 1141. Through the configuration, the gate dielectric layer 1141 separates the semiconductor layers 1142 from the gate electrodes G. In some embodiments of the present invention, the gate electrodes G, the gate dielectric layer 1141, the semiconductor layers 1142, and the source and drain electrodes S and D constitute the active devices 114a, 114b, 114c. The active devices 114a, 114b, 114c may be field effect transistor (FET), such as Metal-Oxide-Semiconductor FET (MOSFET). The active devices 114a, 114b, 114c may be form by the same thin-film fabrication process. The gate electrodes G overlaps a channel layer (e.g., a portion of the semiconductor layers 1142) in a vertical direction, and the source and drain electrodes S and D are connected to two ends of the channel layer, respectively. Through the configuration, the gate electrode G may be controlled to conduct the channel layer, such that an electric conduction between the source electrode and the drain electrode are established. In some embodiments, the active devices 114a, 114b, and 114c may be a bottom gate structure (i.e., the channel layer is over the gate electrode G) or a top gate structure (i.e., the gate electrode G is over the channel layer). The structure and formation methods of the active devices 114b are similar to those of the active devices 114a and 114c, and not repeated herein.

In some embodiments of the present invention, the passivation layer 1143 covers the active devices 114a-114c. The bottom electrode 1144 is over the passivation layer 1143 and connected to the source electrode S of the active device 114a through a conductive via in the passivation layer 1143. The bottom electrode 1144 may include suitable transparent or opaque conductive material, such as metal, for example, Cu, Mo/Al/Mo, Mo/Al—Nd/Mo, or the like. The passivation layer 1145 covers the active devices 114a-114c and exposes the bottom electrode 1144. The light-sensing structure PDS is disposed over the exposed bottom electrode 1144. The light-sensing structure PDS may be a PN junction diode structure, a PIN junction diode structure, or other suitable structures. The top electrode 1146 is disposed over the light-sensing structure PDS. The top electrode 1146 includes a transparent conductive material, such as indium tin oxide (ITO) or metal mesh, such that the light generated by the X-ray conversion layer 130 may pass through the top electrode 1146 and reach the light-sensing structure PDS. As such, the top electrode 1146, the light-sensing structure PDS, and the bottom electrode 1144 constitute the light-sensing device PD. In addition, the active device array substrate 110 further includes an electrode AD that formed with the bottom electrode 1144 from the same layer. The electrode AD may be connected to the drain electrode D of the active device 114*a* through a conductive via in the passivation layer 1143.

The passivation layer 1147 is disposed on the light-sensing device PD. The signal lines DL1-DL5 and the bias line BS are disposed over the passivation layer 1147, and the signal lines DL1-DL5 are connected to the electrode AD through a conductive via in the passivation layer 1147. Through the configuration, the signal lines DL1-DL5 are electrically connected to the drain electrodes D of the active devices 114*a*. The bias line BS is connected to the top electrode 1146 through a conductive via in the passivation layer 1147. The signal lines DL1-DL5 and the bias line BS may include suitable conductive material, such as metal, for example, Cu, Mo/Al/Mo, Mo/Al—Nd/Mo, or the like. The signal lines DL1-DL5 and the bias line BS may be formed by the same fabrication process. For example, the fabrication process includes patterning a metal layer to form the signal lines DL1-DL5 and the bias line BS. Afterward, a passivation layer 1148 may be disposed on the signal lines DL1-DL5 and the bias line BS for protecting the signal lines DL1-DL5 and the bias line BS. In some embodiments of the present invention, the passivation layers 1143, 1145, 1147, and 1148 include suitable insulating material, such as silicon nitride, silicon oxide, or the like.

In some embodiments of the present invention, the signal control circuit 115 and the scan control circuit 116 may be plural integrated circuit (IC) chips. The IC chips may include plural pins connected with the signal lines DL1-DL5, the scan lines SL1-SL5, and/or the control signal lines SW1 and SW2. The signal control circuit 115 and the scan control circuit 116 are electrically connected with each other, for example, by one or more conductive wires WL, such that signals may be synchronized. In some embodiments, the signal control circuit 115 and the scan control circuit 116 may be disposed in a single IC chip. In the present embodiments, the driver chips are arranged by Chip-on-Glass (COG) bonding technique, but it should not limit the scope of the present invention. In some other embodiments, the Chip-on-Film (COF) bonding technique or Tape Carrier Package (TCP) bonding technique may be adopted.

Figure 3:
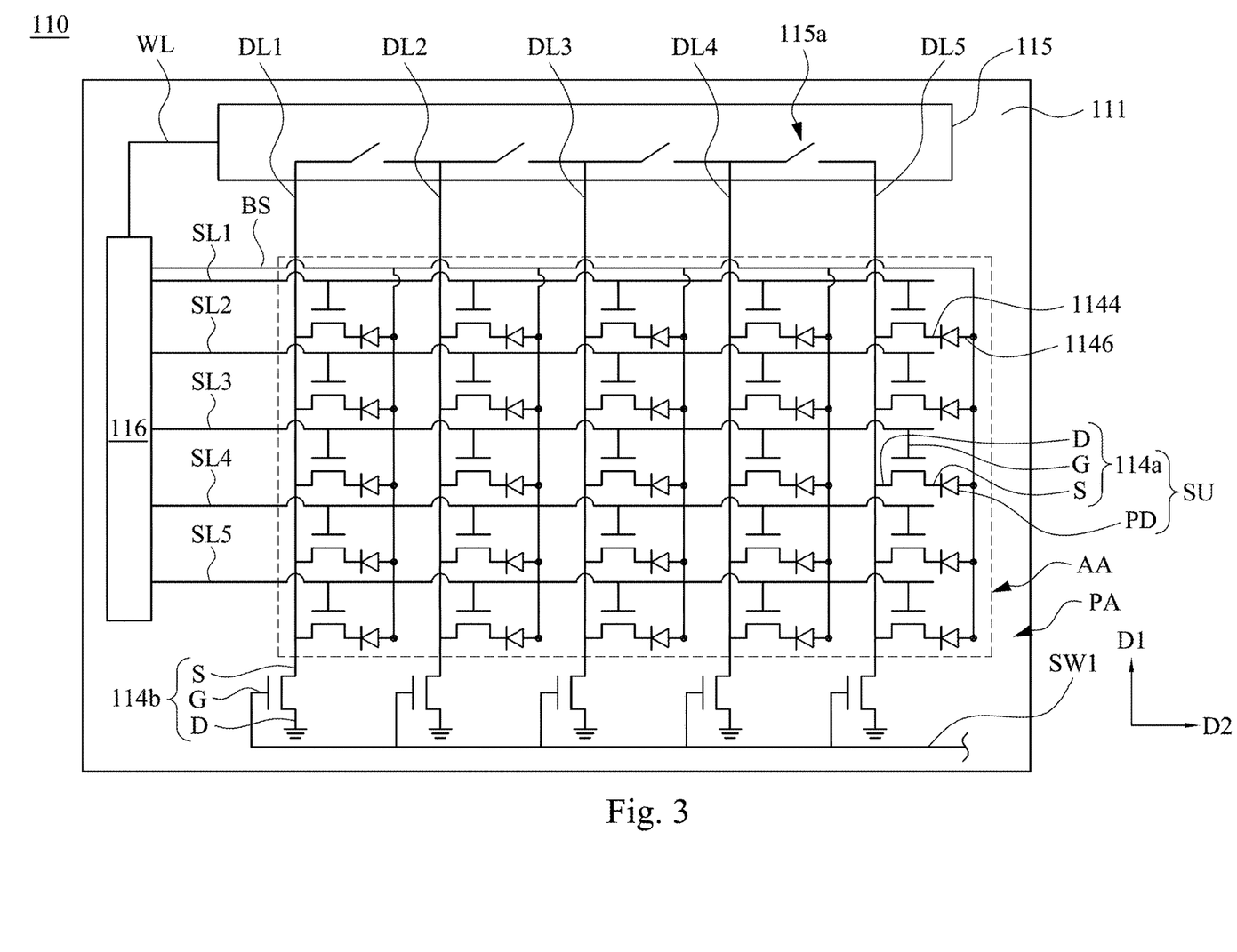
FIG. 3 is a schematic top view of an X-ray detector according to some embodiments of the invention.

FIG. 3 is a schematic top view of an X-ray detector according to some embodiments of the invention. The present embodiments are similar to the embodiments of FIG. 2A, and the difference between the present embodiments and the embodiments of FIG. 2A is that: in the present embodiments, at least one of the signal control circuit 115 and the scan control circuit 116 is configured establish a conduction between plural signal lines DL1-DL5, such that the plural signal lines DL1-DL5 are shorted. For example, the signal control circuit 115 has a built-in switch 115*a* connecting at least two of the signal lines DL1-DL5 to each other, in which the built-in switch 115*a* is capable of selectively establish a conduction between the two of the signal lines DL1-DL5. To be specific, in a certain time range, the control circuit may turn on the switches 115*a* simultaneously to electrically connect all the signal lines DL1-DL5 to each other, and in the time range, the active devices 114*a* are turned on by the scan lines SL1-SL5 simultaneously, such that the electrodes of the light-sensing devices PD are electrically connected with each other and shorted, which in turn will make the residual charges in the light-sensing devices PD uniform. Other details of the present embodiments are similar to those aforementioned, and not repeated herein.

Figure 4:
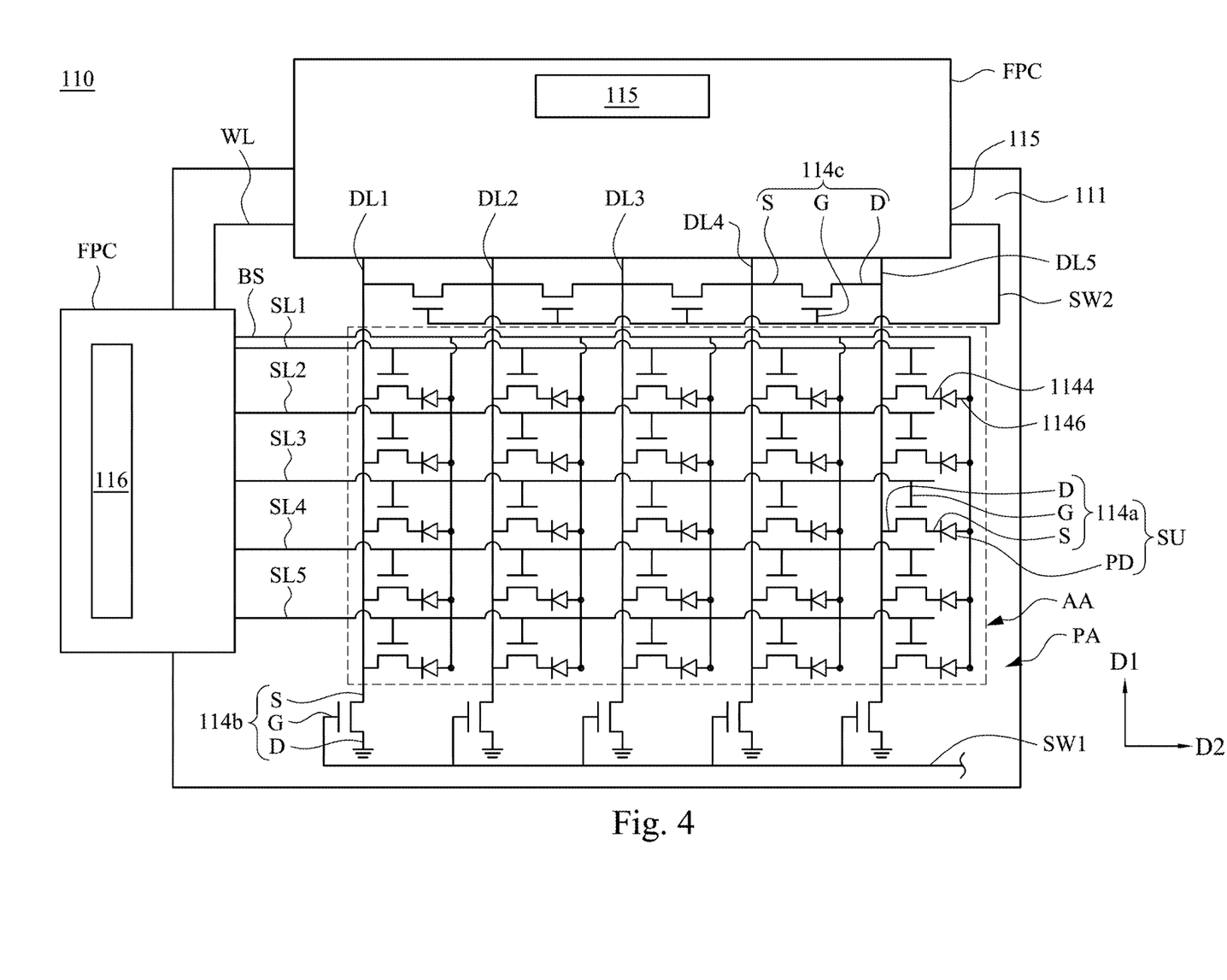
FIG. 4 is a schematic top view of an X-ray detector according to some embodiments of the invention.

FIG. 4 is a schematic top view of an X-ray detector according to some embodiments of the invention. The present embodiments are similar to the embodiments of FIG. 2A, and the difference between the present embodiments and the embodiments of FIG. 2A is that: in the present embodiments, the X-ray detector 100 further includes a flexible printed circuit board FPC, and the signal control circuit 115 and the scan control circuit 116 may be chips disposed on the flexible printed circuit board FPC and electrically connected with the signal lines DL1-DL5 and scan lines SL1-SL5 through circuits on the flexible printed circuit board FPC. In the present embodiments, the driver chips are arranged by Chip-on-Film (COF) bonding technique. Other details of the present embodiments are similar to those aforementioned, and not repeated herein.

Figure 5:
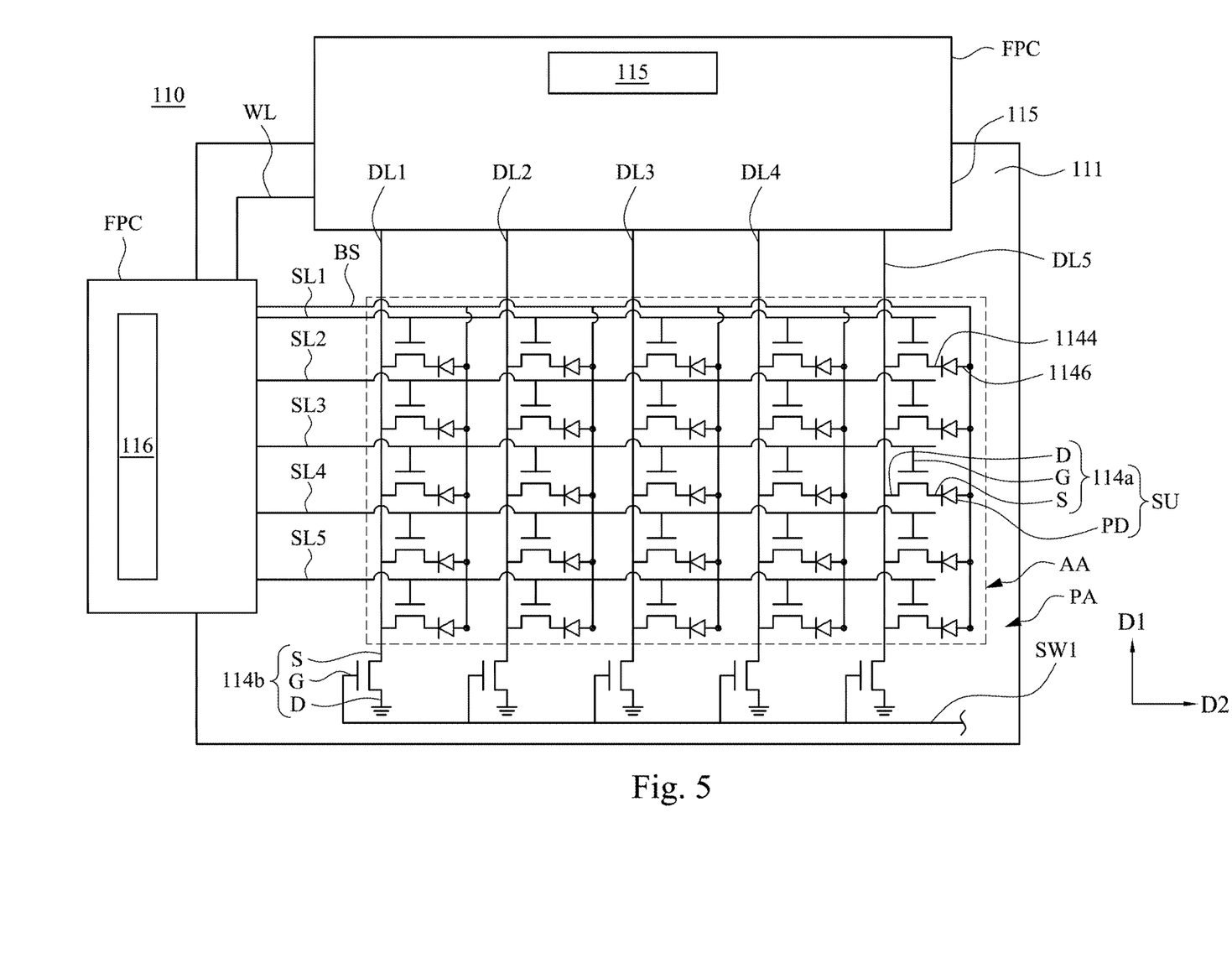
FIG. 5 is a schematic top view of an X-ray detector according to some embodiments of the invention.

FIG. 5 is a schematic top view of an X-ray detector according to some embodiments of the invention. The present embodiments are similar to the embodiments of FIG. 3, and the difference between the present embodiments and the embodiments of FIG. 3 is that: in the present embodiments, the X-ray detector 100 may further include a flexible printed circuit board FPC, and the signal control circuit 115 and the scan control circuit 116 may be chips disposed on the flexible printed circuit board FPC and electrically connected with the signal lines DL1-DL5 and scan lines SL1-SL5. In the present embodiments, the driver chips are arranged by Chip-on-Film (COF) bonding technique. Other details of the present embodiments are similar to those aforementioned, and not repeated herein.

Figure 6:
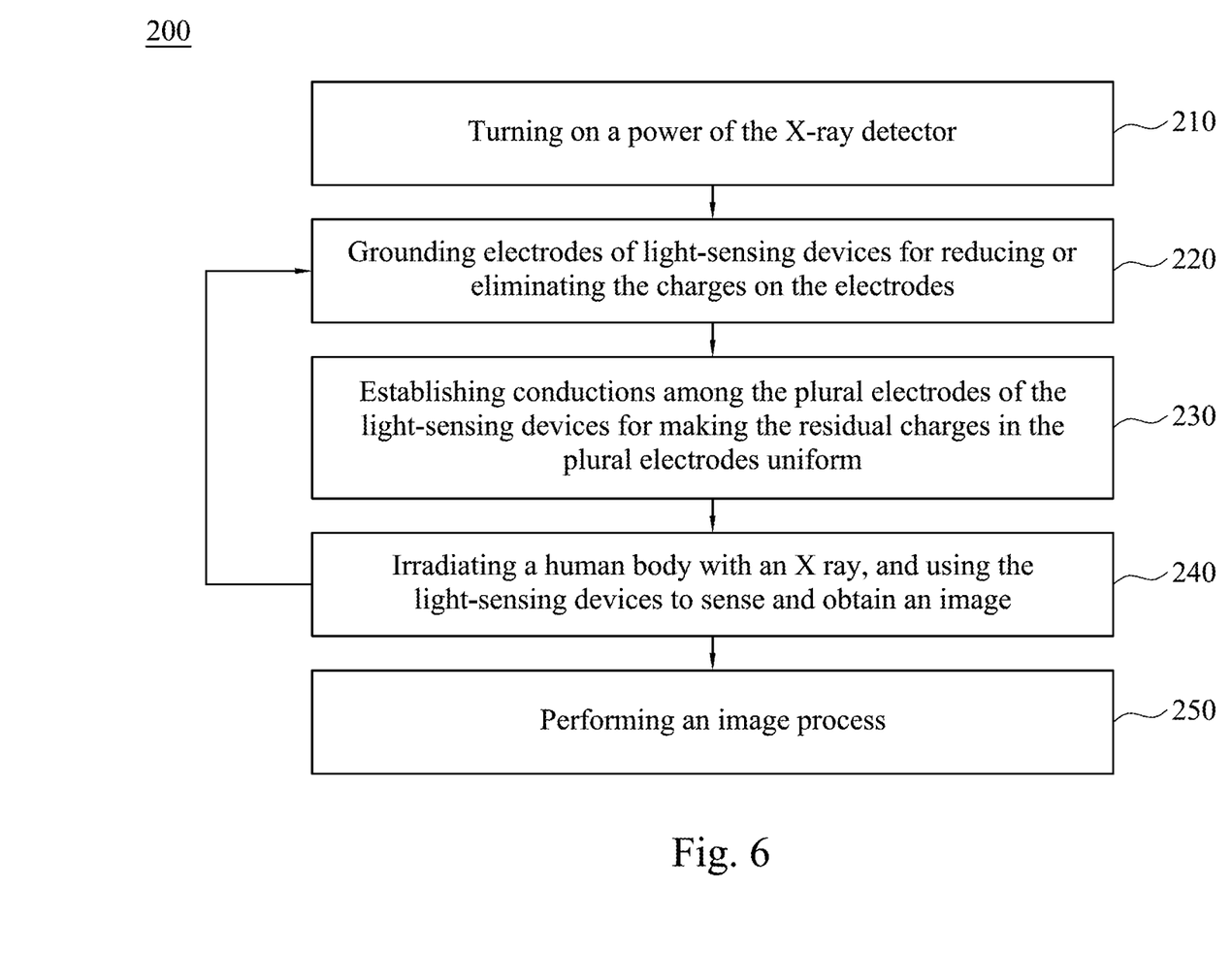
FIG. 6 is a flow chart of a method for processing residual charges in an X-ray detector according to some embodiments of the invention.

FIG. 6 is a flow chart of a method 200 for processing residual charges in an X-ray detector according to some embodiments of the invention. The method 200 is illustrated with reference to the X-ray detector in FIG. 1A and FIG. 2A or in FIG. 3.

The method 200 begins with step 210, where a power of the X-ray detector 100 is turned on, such that the signal control circuit 115 and the scan control circuit 116 can operate. In some embodiments, this step may include using the bias line BS provide suitable DC (direct current) bias to the top electrode 1146 of the light-sensing device PD (referring to FIG. 1B and FIG. 2A), which facilitates the current output of the light-sensing device PD.

Subsequently, the method proceeds to step 220, where the bottom electrodes 1144 of the light-sensing devices PD are grounded for removing residual charges on the electrodes 1144. In the present embodiments, the signal control circuit 115 or the scan control circuit 116 emits control signals to turn on the active devices 114*b* through the control signal line SW1 and turn on the active devices 114*a* through the scan lines SL1-SL5, such that the electrodes 1144 of the light-sensing devices PD is grounded through the active devices 114*b*. Through this step, the charges in the electrodes 1144 of the light-sensing device PD are reduced or eliminated. In this step, the active devices 114*c* are at off state. For example, the signal control circuit 115 or the scan control circuit 116 emits control signals to keep the active devices 114*c* at off state through the control signal line SW2. Alternatively, the switch 115*a* is at off state, and does not conduct.

However, in some cases, a ground potential may be set on other component (e.g., a flexible printed circuit board or a printed circuit board), such that a path from the light-sensing device PD to the ground potential may be too long to entirely eliminate charges on the electrodes 114, which in turn will leave residual charges on the electrodes 1144. Furthermore, the light-sensing devices PD at different positions have different paths to the ground potential, such that the charges of the light-sensing devices PD are reduced by different amount through grounding, which in turn will result in the light-sensing devices PD have different amounts of residual charges. The different amounts of the residual charges at different locations create a burden of following image processing for improving image quality.

In some embodiments of the present invention, the method 200 proceeds to step 230, where conductions among the plural electrodes 1144 of the light-sensing devices PD are established by the signal lines DL1-DL2 by using the aforementioned transistors 114c or switches 115a. Through the configuration, the plural electrodes 1144 of the light-sensing devices PD are electrically connected and shorted with each other, which in turn will make the residual charges in the plural electrodes 1144 uniform. In the present embodiments, the signal control circuit 115 or the scan control circuit 116 emits control signals to turn on the active devices 114c through the control signal line SW2 and turn on the active devices 114a through the scan lines SL1-SL5, such that the electrodes 1144 of the light-sensing devices PD are electrically connected with each other by the active devices 114a and 114c, which in turn will make the residual charges in the plural electrodes 1144 of the light-sensing device PD (referring to FIG. 2C) uniform. Alternatively, in some embodiments, the switches 115a conduct, such that the electrodes 1144 of the light-sensing devices PD are electrically connected with each other by the switches 115a. Through this step, the difference between the amounts of the residual charges in the electrodes 1144 of the light-sensing devices PD (referring to FIG. 2C) at different locations is reduced. At this step 230, the active devices 114b are at off state. For example, the signal control circuit 115 or the scan control circuit 116 emits control signals to keep the active devices 114b at off state through the control signal line SW1. In other words, at this step 230, the electrodes 1144 of the light-sensing devices PD (referring to FIG. 2C) are not grounded.

Then, the method proceeds to step 240, where a human body is irradiated by an X ray. The aforementioned X-ray conversion layer 130 converts the X ray to light, and the light-sensing device PD receives the light and convert the light into electrons. The electric signals on the electrodes 1144 of the respective light-sensing device PD may be retrieved via the signal lines DL1-DL5 by the scanning using the scan lines SL1-SL5, thereby obtaining an image. In the present embodiments, the step 240 may be performed by turning off the control signal lines SW1 and SW2 and providing suitable voltages to the scan lines SL1-SL5. The signals on the electrodes 1144 of the light-sensing device PD may be sent to the signal control circuit 115 through the signal lines DL1-DL5 time-sequentially by the scanning control using the scan lines SL1-SL5. Prior to this step 240, the signal control circuit 115 or the scan control circuit 116 emits signals to the control signal line SW2 to stop the conduction of the active devices 114c, so as to terminate the conduction between the electrodes 1144. As such, when the step 240 is performed, through the control of the control signal line SW1, the active devices 114b do not conduct, such that the electrodes 1144 are not grounded; and through the control of the control signal line SW2, the active devices 114c do not conduct, such that the electrodes 1144 are not shorted.

Figure 7A:
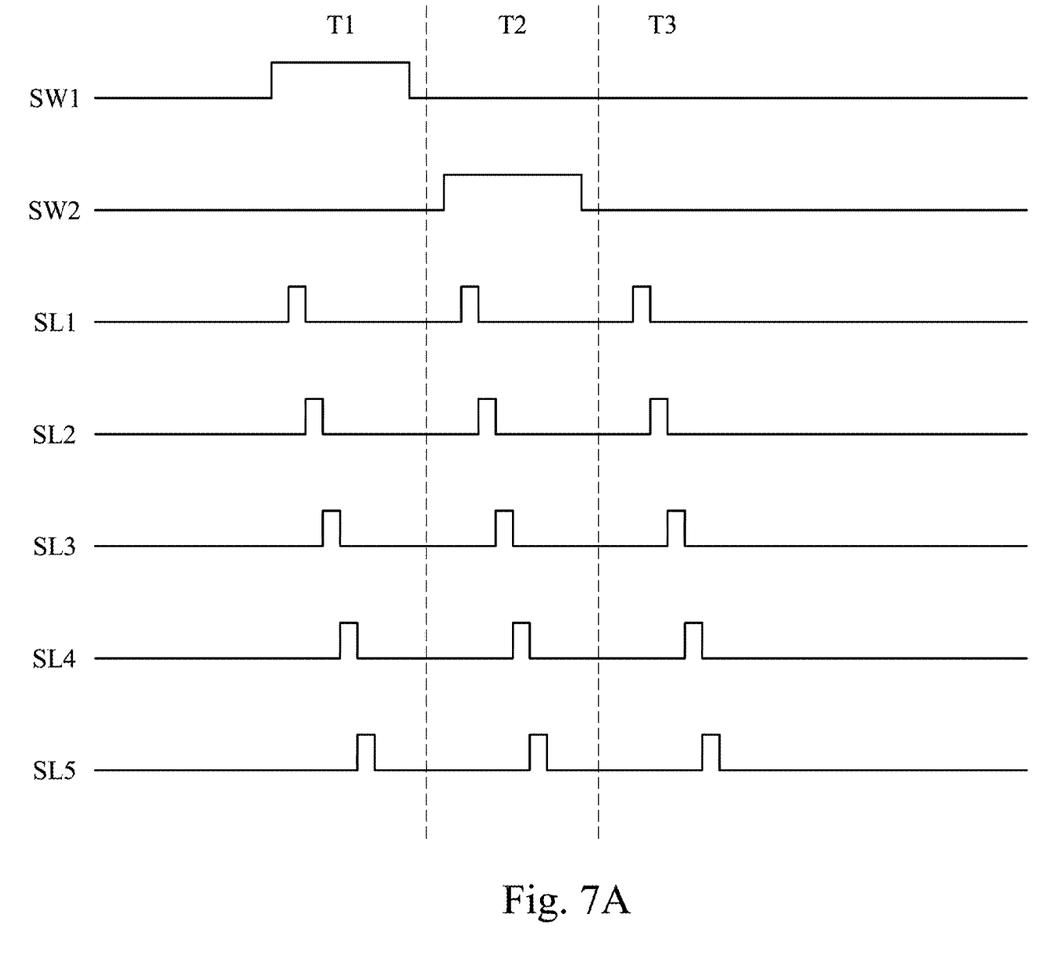
FIG. 7A is a wave diagram of scan signals and control signals at various operation timings according to some embodiments of the invention.
Figure 7B:
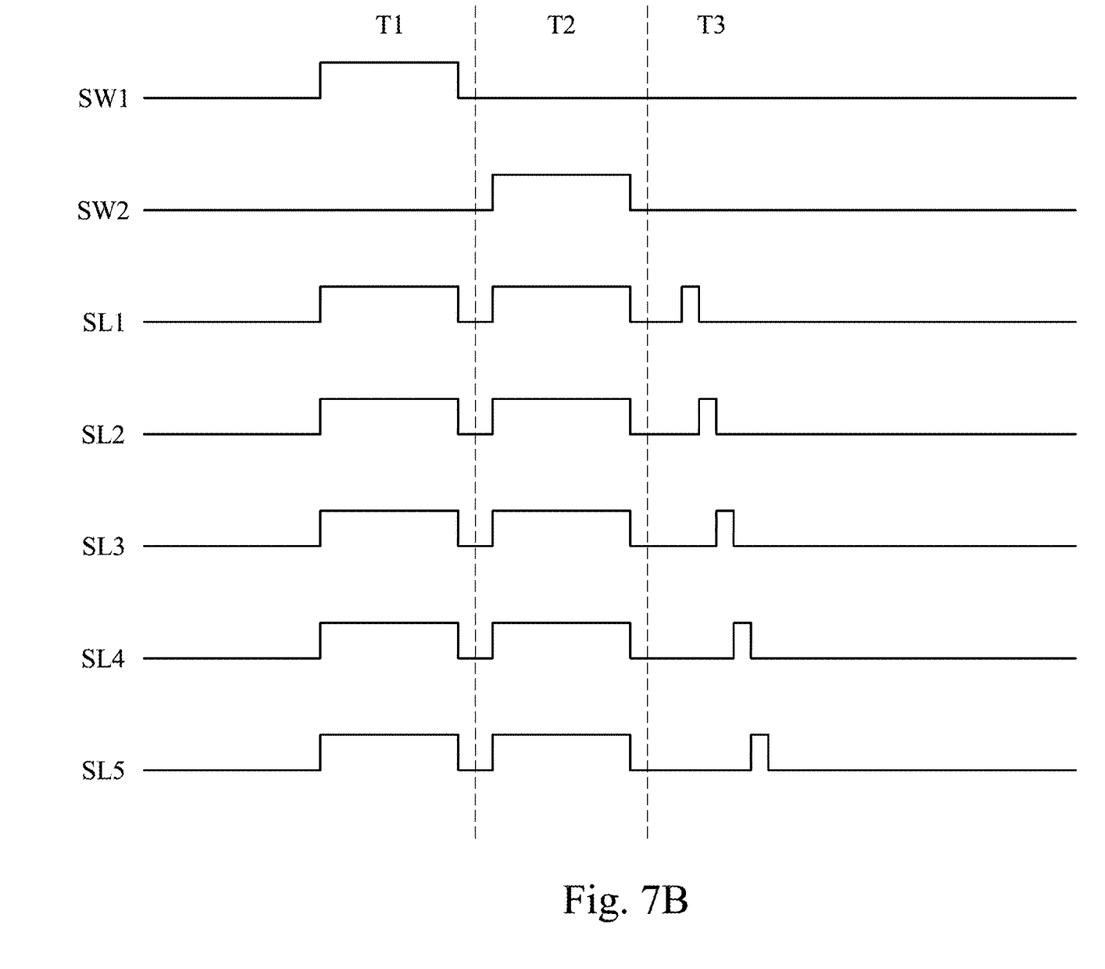
FIG. 7B is a wave diagram of scan signals and control signals at various operation timings according to some embodiments of the invention.

In the present embodiments, the steps 220-230 may be performed by turning on the scan lines SL1-SL5 and providing suitable voltages to the control signal lines SW1 and SW2. Furthermore, the electrodes 1144 of the light-sensing device PD are grounded or electrically connected to each other according to a time-sequential scanning of the control signal lines SW1 and SW2. FIG. 7A is a wave diagram of scan signals and control signals at various operation timings according to some embodiments of the invention. In the present example, the step 220 is performed at timing T1, the step 230 is performed at timing T2, and the step 240 is performed at timing T3. At the timing T1, the control signal line SW1 is turned on, and the control signal line SW2 is turned off, and the scan lines SL1-SL5 are turned on sequentially, so as to achieve the purpose of grounding the electrodes 1144 of the light-sensing device PD. At the timing T2, the control signal line SW1 is turned off, and the control signal line SW2 is turned on, and the scan lines SL1-SL5 are turned on sequentially, so as to achieve the purpose of making the charge distribution uniform. At the timing T3, the control signal line SW1 is turned off, and the control signal line SW2 is turned off, and the scan lines SL1-SL5 are turned on sequentially, so as to retrieve the sensing information of the light-sensing device PD by scanning. Herein, at the timings T1/T2, the scan lines SL1-SL5 are turned on in a scanning way. However, it should not limit the scope of the present invention. FIG. 7B is a wave diagram of scan signals and control signals at various operation timings according to some embodiments of the invention. In the embodiments of FIG. 7B, at the timings T1/T2, the scan lines SL1-SL5 are turned on at the same time, but not limited to be turned on sequentially in the scanning way.

Afterwards, the method proceeds to the step 250, where the signals of the image is adjusted. Herein, since the distribution of residual charges has been improved to be more uniform by the step 230, the influence of the residual charges on the image is more uniform, and has small variation at different locations. As such, the image quality may be improved by uniformly adjusting the respective pixels of the image. For example, in case that the influence of residual charges may be too huge to calibrate the image to an acceptable image quality, the entire image may be adjusted by an offset method, and then adjusted by the calibration method.

In some embodiments, after obtaining the image (i.e., the step 240), a process for capturing a next image is performed. Before capturing the next image, the step 220 is performed for reducing or eliminating the residual charges in the electrodes 1144 left by previous capturing process, and the step 230 is repeated for improving the uniformity of the charge distribution. Then, the next image is captured and obtained (i.e., the next step 240).

In some embodiments of the present invention, the active device array substrate is designed to have active devices connected to various signal lines and control signal lines configured to control the active devices. Through the configuration, by controlling the various scan lines and the control signal lines, the electrodes of the light-sensing device may be grounded, electrically connected to each other, or capable of sending signals to the signal lines at different timings. By electrically connecting the electrodes of the light-sensing device to each other (i.e., establishing a conduction between the electrodes), the difference between the amounts of the residual charges at difference locations is reduced. Furthermore, by uniformly adjusting the respective pixels of the image, the image quality is improved.

Although the present invention has been described in considerable detail with reference to certain embodiments thereof, other embodiments are possible. Therefore, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. An X-ray detector, comprising:
   a substrate;
   a plurality of signal lines disposed on the substrate;
   a plurality of scan lines disposed on the substrate and intersecting with the signal lines;
   a plurality of sensing units electrically connected to the signal lines and the scan lines; and
   a first active device having a first terminal, a second terminal, and a control terminal configured to modulate a conduction between the first terminal and the second terminal, wherein the first terminal of the first active device is connected to a first one of the signal lines, and the second terminal of the first active device is connected to a second one of the signal lines.

2. The X-ray detector of claim 1, further comprising:
   a control signal line; and
   a control circuit, wherein the control signal line connects the control terminal of the first active device to the control circuit.

3. The X-ray detector of claim 2, wherein the signal lines are connected to the control circuit.

4. The X-ray detector of claim 1, further comprising:
   a second active device having a first terminal, a second terminal, and a control terminal configured to modulate a conduction between the first terminal of the second active device and the second terminal of the second active device, wherein the first terminal of the second active device is connected to the second one of the signal lines, and the second terminal of the second active device is connected to a third one of the signal lines.

5. The X-ray detector of claim 4, further comprising:
   a control signal line connecting the control terminal of the first active device and the control terminal of the second active device.

6. The X-ray detector of claim 1, further comprising:
   a third active device having a first terminal, a second terminal, and a control terminal configured to modulate a conduction between the first terminal of the third active device and the second terminal of the third active device, wherein the first terminal of the third active device is connected to the first one of the signal lines, and the second terminal of the third active device is connected to a ground potential.

7. The X-ray detector of claim 6, further comprising:
   a control signal line; and
   a control circuit, wherein the control signal line connects the control terminal of the third active device to the control circuit.

8. The X-ray detector of claim 1, wherein each of the sensing units comprises a light sensing element.

9. The X-ray detector of claim 1, further comprising:
   an X-ray conversion layer, wherein the sensing units are between the X-ray conversion layer and the substrate.

10. The X-ray detector of claim 1, wherein the substrate has an array area and a peripheral area at at least one side of the array area, the sensing units are over the array area of the substrate, and the first active device is over the peripheral area of the substrate.

11. An X-ray detector, comprising:
    a substrate;
    a plurality of signal lines disposed on the substrate;
    a plurality of scan lines disposed on the substrate and intersecting with the signal lines;
    a plurality of sensing units electrically connected to the signal lines and the scan lines; and
    a control circuit connected between the signal lines, wherein the control circuit is configured to establish an electrical conduction between a first one of the signal lines and a second one of the signal lines at a first timing without grounding said first one of the signal lines and said second one of the signal lines and terminate the electrical conduction between said first one of the signal lines and said second one of the signal lines at a second timing different from the first timing, such that said first one of the signal lines is electrically disconnected from said second one of the signal lines at the second timing.

12. The X-ray detector of claim 11, wherein the control circuit is configured to ground the first one of the signal lines at the second timing.

13. The X-ray detector of claim 11, wherein the control circuit is disposed on the substrate.

14. A method for capturing an image by an X-ray detector, comprising:
    establishing an electrical conduction between a first electrode of a first light sensing element and a second electrode of a second light sensing element without grounding the first electrode of the first light sensing element and the second electrode of the second light sensing element;
    terminating the electrical conduction between the first electrode of the first light sensing element and the second electrode of the second light sensing element; and
    detecting light by using the first light sensing element and the second light sensing element to obtained an image when the first electrode of the first light sensing element is electrically disconnected from the second electrode of the second light sensing element.

15. The method of claim 14, further comprising:
    performing a correction process to the image.

16. The method of claim 14, further comprising:
    grounding the first and second electrodes when the first electrode of the first light sensing element is electrically disconnected from the second electrode of the second light sensing element.

17. The method of claim 14, further comprising:
    establishing an electrical conduction between a third electrode of a third light sensing element and the second electrode of the second light sensing element.

18. The method of claim 17, wherein establishing the electrical conduction between the first and second electrodes and establishing the electrical conduction between the second and third electrodes comprise:
    turning on a first active device and a second active device, wherein the first active device is connected between the first electrode and the second electrode, and the second active device is connected between the second electrode and the third electrode.

* * * * *